United States Patent
Rump et al.

(10) Patent No.: US 10,285,609 B2
(45) Date of Patent: May 14, 2019

(54) IMPLANTABLE DEVICE AND PRODUCTION METHOD FOR AN IMPLANTABLE DEVICE

(71) Applicant: BIOTRONIK SE & CO. KG, Berlin (DE)

(72) Inventors: Jens Rump, Berlin (DE); Michael Friedrich, Kleinmachnow (DE); Heinrich Buessing, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 1167 days.

(21) Appl. No.: 14/463,477

(22) Filed: Aug. 19, 2014

(65) Prior Publication Data

US 2015/0057521 A1    Feb. 26, 2015

Related U.S. Application Data

(60) Provisional application No. 61/869,768, filed on Aug. 26, 2013.

(51) Int. Cl.
*A61B 5/04*     (2006.01)
*A61B 5/042*    (2006.01)
(Continued)

(52) U.S. Cl.
CPC ............... *A61B 5/042* (2013.01); *A61N 1/05* (2013.01); *A61N 1/056* (2013.01); *A61N 1/365* (2013.01); *A61N 1/3718* (2013.01); *A61N 1/3925* (2013.01); *A61N 1/086* (2017.08); *Y10T 29/49117* (2015.01)

(58) Field of Classification Search
CPC ....... A61B 5/042; A61B 5/044; A61B 5/6852; A61B 5/686; A61B 5/6867; A61B 5/6868; A61B 5/6869; A61N 1/056; A61N 1/3718; A61N 1/05; A61N 1/365; A61N 1/3925; A61N 1/0526; A61N 1/0529;
(Continued)

(56) References Cited

U.S. PATENT DOCUMENTS 4,355,646 A * 10/1982 Kallok ................. A61N 1/056
607/122
5,609,622 A * 3/1997 Soukup ................ A61N 1/056
607/122
(Continued)

FOREIGN PATENT DOCUMENTS

ES     2211325 A1    7/2004

OTHER PUBLICATIONS

European Search Report received in EP Application Serial No. 14174640, dated Mar. 4, 2015, 6 pages.

*Primary Examiner* — Eun Hwa Kim
(74) *Attorney, Agent, or Firm* — Arc IP Law, PC; Joesph J. Mayo

(57) ABSTRACT

Embodiments of the invention include a temporarily or permanently implantable medical device with an elongate electrical line, and a method of producing the implantable medical device. The elongate electrical line includes a first electrical component and a second component, wherein the first electrical component or part of the first electrical component includes a functional conductor. The second component includes at least one metal layer and at least one flexible plastic layer. The first electrical component is electrically connected in series to the at least one metal layer of the second component.

14 Claims, 7 Drawing Sheets

(51) Int. Cl.
*A61N 1/05* (2006.01)
*A61N 1/365* (2006.01)
*A61N 1/39* (2006.01)
*A61N 1/37* (2006.01)
*A61N 1/08* (2006.01)

(58) Field of Classification Search
CPC .. A61N 1/0531; A61N 1/0534; A61N 1/0536; A61N 1/0587; Y10T 29/49117
See application file for complete search history.

(56) References Cited

U.S. PATENT DOCUMENTS

| | | |
|---|---|---|
| 6,871,091 B2 | 3/2005 | Wilkinson |
| 7,904,178 B2 | 3/2011 | Williams |
| 8,380,322 B2 | 2/2013 | Taeubert et al. |
| 2008/0140156 A1 | 6/2008 | Rodriguez et al. |
| 2008/0167701 A1 | 7/2008 | John et al. |
| 2009/0163981 A1* | 6/2009 | Stevenson ............ A61N 1/025 607/63 |
| 2011/0196229 A1 | 8/2011 | Weiss et al. |
| 2013/0103106 A1* | 4/2013 | Schotzko ............ A61N 1/3686 607/2 |

* cited by examiner

IMPLANTABLE DEVICE AND PRODUCTION METHOD FOR AN IMPLANTABLE DEVICE

This application claims the benefit of U.S. Provisional Patent Application 61/869,768, filed on 26 Aug. 2013, the specification of which is hereby incorporated herein by reference.

BACKGROUND OF THE INVENTION

Field of the Invention

Embodiments of the invention generally relate to a permanently or temporarily implantable medical device with an elongate electrical conductor, and a production method for an implantable medical device.

Description of the Related Art

Generally, medical devices containing electrical conductors, for example electrode lines for electro-stimulation or electrodes for cardiac pacemakers, have a disadvantage that the electrical conductor may heat up in an electromagnetic alternating field, for example in an MRI scanner, since electromagnetic alternating fields typically induce electrical currents in the electrical conductor. Typically, the heating occurs at ends of electrode lines and is dependent on the amplitude of the waves of the electromagnetic alternating fields, wherein the heating is generally greatest with formation of standing waves.

Implantable cardiac pacemakers or defibrillators are typically connected to at least one stimulation electrode line. A distal end of a stimulation electrode line, which is typically placed in a heart, generally includes one or more electrode poles. Such electrode poles, generally, are used to deliver electrical pulses, for example to the heart tissue (myocardium), or to sense electrical fields in order to sense activity, for example cardiac activity, from the heart tissue, within the scope of what is known as "sensing".

Generally, two electrode poles typically form electrically conductive surface portions of an electrode line. The electrode poles are typically provided as ring electrodes in the form of a ring around the electrode line or in the form of a point electrode or tip electrode at the distal end of the electrode line. The electrode poles are generally electrically conductively connected, via one or more electrical conductors, to contacts of an electrical terminal of the electrode line at the proximal ends thereof. Typically, the electrical conductors may be used for transmission of stimulation pulses to the electrode poles and/or for transmission of electrical signals, received by the electrode poles, to the proximal end of the electrode line. Generally, electrical conductors of the electrode line (that is to say the primary function of the electrode line) are referred to within the scope of this text as functional conductors.

Typically, via external alternating magnetic fields, electrical currents may be induced into the functional conductors, and for example may lead to heating of the functional conductors and/or of the electrode poles connected thereto. If the functional conductors are connected to electrode poles, which may have contact with surrounding tissue during operation, the induction of currents in a functional conductor may generally lead to heating of the electrode poles connected to the functional conductors and to heating of the surrounding tissue.

U.S. Pat. No. 7,904,178 to Williams et al., entitled "Medical Electrical Lead Body Designs Incorporating Energy Dissipating Shunt", discloses an elongate body of a medical electrical lead including at least one conductor formed into a coil. According to Williams et al., the conductor includes a first portion extending within an outer insulation sleeve, and a second portion, which extends outside the outer insulation sleeve, used as an energy-diverting shunt.

U.S. Pat. No. 6,871,091 to Wilkinson et al., entitled "Apparatus and Method for Shunting Induced Currents In An Electrical Lead", discloses an electrical lead with an elongate body. According to Wilkinson et al., the electrical lead includes distal and proximal end portions, a first electrode connected to the distal end portion of the elongate body and a first conductor extending between the distal and proximal end portions, wherein the conductor is electrically connected to the first electrode. The system of Wilkinson et al. also includes a second electrode connected to the elongate body, and a capacitor electrically connected to the first conductor and the second electrode.

BRIEF SUMMARY OF THE INVENTION

One or more embodiments of the invention are related to an implantable medical device with an electrode line and a method of producing the implantable medical device, wherein heating of the electrode line and/or of the tissue in contact with the electrode line is reduced. In at least one embodiment, the method of production of the implantable medical device is a reliable and cost-effective production of a miniaturized implantable medical device. At least one embodiment of the invention includes an implantable medical device with reduced heating of the electrode line and/or of the tissue in contact with the electrode line and increased mechanical and electrical stability, and wherein the implantable medical device includes a hermetic design with sparse use of different material groups.

This is achieved in accordance with at least one embodiment of the invention by a temporarily or permanently implantable medical device including at least one elongate electrical line, which contains a functional conductor as a first electrical component or as part of a first electrical component. In at least one embodiment, the first electrical component of the medical device is in electrical contact with at least a second component. In one or more embodiments, the second component may include a composite formed from at least one metal layer and at least one flexible plastic layer. In at least one embodiment, at least one of the metal layers of the second component may be connected in series to the first electrical component.

In one or more embodiments, at least one metal layer of the second component is connected in series to an electrode or to the first electrical component, such that electromagnetic waves in a radio frequency range may be reflected back, and heating of the tissue at the distal end of the medical device or in the vicinity of the distal end of the medical device is therefore reduced. In at least one embodiment, the implantable medical device includes a simple and compact design with high mechanical stability, for example in a direction of pull, and simplifies the electrical connection to an electrode, such as to a wire helix or inner helix of the electrode. One or more embodiments of the invention may include at least one plastic layer to hermetically seal conductive parts of the implantable medical device, such that effects of electrolytic liquids may be eliminated, and selection of usable elements of the at least one metal layer may be extended.

According to at least one embodiment, a production method for the implantable medical device includes one or more of providing a first electrical component, such as an electrical line, and at least one second component with at least one metal layer. The electrical line, in at least one embodiment, may include a functional conductor as the first electrical component or as part of the first electrical component. In one or more embodiments, at least one second component may include at least one flexible plastic layer, wherein the at least one metal layer of the second component may be connected to the at least one flexible plastic layer. In at least one embodiment, the at least one metal layer of the at least one second component may be connected to the first electrical component in a series connection. In one or more embodiments, a plurality of second components may be connected in series.

By way of at least one embodiment of the production method a miniaturized implantable medical device is produced, wherein electromagnetic waves in the radio-frequency range are reflected back by the at least one metal layer of the second component connected in series to the first electrical component. As such, in at least one embodiment, the heating of the tissue, for example at the distal end of the medical device or in the vicinity of the distal end of the medical device, is reduced. One or more embodiments of the production method also enables automation with low susceptibility to production tolerances, to enable cost-effective and flexible production of the implantable medical device. At least one embodiment of the invention includes a secure electrical connection between the first and second components, with small or large dimensioning (>10 mm), wherein the implantable medical device may be miniaturized by division.

In at least one embodiment, the implantable medical device may be an electrode line or part of an electrode line. The electrode line, in one or more embodiments, may be connected via a terminal to a therapy and/or monitoring device. In at least one embodiment, the implantable medical device may be part of the therapy and/or monitoring device.

According to at least one embodiment of the invention, the at least one metal layer includes a first width, and the second component includes a second width, wherein the first width of the at least one metal layer of the second component is less than the second width of the at least one flexible plastic layer, wherein the second component may include at least one electrically non-conductive plastic edge. In one or more embodiments, the electrically non-conductive plastic edge may be provided on one side or on at least two sides of the second component. In at least one embodiment, each of the electrically non-conductive plastic edges may include a different plastic from the at least one flexible plastic layer and/or may be applied to the at least one flexible plastic layer. In one or more embodiments, the at least one metal layer of the at least one second component may be surrounded by one or more plastic layers, for example in a sandwich construction or the like. In at least one embodiment, the at least one metal layer may be embedded in a plastic layer or may be applied to a plurality of plastic layers.

According to one or more embodiments, the plastic layer is a flexible plastic, which may be wound into a cylinder shape or about a cylinder without damaging the second component. In at least one embodiment, the at least one flexible plastic layer of the second component may include one or more polymers, for example one or more of polyester, polyimide, polyamide, polytetrafluroethylene, polypropylene, polyurethane or the like.

By way of one or more embodiments, the at least one metal layer may be formed such that a winding, for example in a cylinder shape, does not interrupt the electrical line along the at least one metal layer. In at least one embodiment, the at least one metal layer may include one or more metals, for example one or more of gold, silver or the like.

In at least one embodiment, the at least one metal layer of the second component may be applied in a meandering manner onto the at least one flexible plastic layer. The at least one metal layer, in one or more embodiments, may be applied in various other forms, for example in a zigzagged manner, spiraled manner, labyrinth manner or the like. According to at least one embodiment, the second component may be flat and may be divided to produce, along an axis perpendicular to a longitudinal axis of the flat second component, identical sub-portions that are electrically conductive along a continuous metal layer to apply the at least one metal layer. In one or more embodiments, the at least one metal layer may be applied with a meander shape, a zigzag shape or the like.

By way of at least one embodiment, the second component may be divided into two or more sub-portions, for example along one or more meander arms, for example at each second meander arm. In one or more embodiments, the second component may be divided physically, for example mechanically, thermally (such as with application of heat), using laser or plasma cautery, and/or chemically (such as by etching or the like). In at least one embodiment, the sub-portions may include cylinder areas, produced by the division, and may be hermetically interconnected by one or more of pressure, heat and a solvent. In one or more embodiments, the metal layers of second components, or of the sub-portions thereof, may be arranged adjacently to one another and for example may be electrically interconnected in a series connection.

In at least one embodiment, the second component may be wound spirally about a longitudinal axis. In one or more embodiments, a plurality of second components may be arranged axially along a longitudinal axis, wound about the longitudinal axis or coaxially about one another. According to at least one embodiment, the at least one metal layer of the wound second component may for example be electrically connected to at least one metal layer of another second component in a series connection. In one or more embodiments, the number of windings may be between 50 and 100, such as between 74 and 76, or may be greater or smaller depending on the thickness and length of the second component. Depending on the shape and winding of the metal layer and the at least one plastic layer contained in the second components, in at least one embodiment, inductors and parasitic capacitors may be connected in parallel thereto and may be adjusted, wherein an implantable medical device with impedances of >1 kOhm with electrical waves in the radio-frequency range may be produced with low quality due to the parasitic capacitors. As such, in one or more embodiments, the implantable medical device may include significantly increased impedance above a maximum impedance in the case of resonance, and may act in a wide-band manner.

In at least one embodiment, the longitudinal axis, about which the second component may be wound, may include a cylinder, a mandrel, a hose, a capillary tube made of plastic, or the like. According to one or more embodiments, by winding the second component about the longitudinal axis, a spiraled line or hollow spiraled line portions may be produced. In at least one embodiment, the second component may also surround the first component. In one or more embodiments, the first component may include a metal sleeve, such as a slit platinum sleeve. One or more embodiments of the invention may include a third component, such as a metal sleeve, that may surround the second component in part or completely. In at least one embodiment, part of the second component may protrude from the third component if the third component is not fully surrounded. In at least one embodiment, the third component may be a slit platinum sleeve with a larger inner diameter than the outer diameter of the wound second component. In one or more embodiments, the second component may be surrounded in part in a wound manner by the platinum sleeve, wherein another part of the second component may protrude from one or more slits in the platinum sleeve. In at least one embodiment, the platinum sleeve may be or may include an electrode or an electrode pole that deliver stimulation pulses or sense electrical potentials, and may be in electrical contact with at least one metal layer of the second component or may be connected in series thereto.

By way of one or more embodiments, the thickness of the at least one metal layer may be less than the width of the at least one metal layer, for example with a thickness between 0.045 µm and 0.300 µm and a width of 1.8 mm.

According to at least one embodiment, the method of producing the implantable medical device may include hermetically interconnecting the edges of the at least one plastic layer of the second component by pressure, heat and/or a solvent.

In one or more embodiments, the method of producing the implantable medical device may include physically dividing at least one portion of the second component into axially arranged sub-portions. In at least one embodiment, the second component may be divided chemically. In one or more embodiments, physical and chemical division of the second component may be implemented simultaneously alongside one another or chronologically one after the other in order to separate the portions of the second component.

One or more embodiments of the invention may include connecting the axially arranged sub-portions of the second component. In at least one embodiment, the axially arranged sub-portions may be hermetically interconnected by pressure, heat and/or solvent. In one or more embodiments, the metal layers of the axially arranged sub-portions may be interconnected in a series connection.

According to at least one embodiment, the implantable medical device may include a proximal side and a distal side. In one or more embodiments, the components within the implantable medical device may include proximal and distal sides. In at least one embodiment, the distal side of the first electrical component may be in contact with a biological body, for example tissue, blood or the like. In one or more embodiments, the first electrical component may transmit stimulation pulses to the biological body. In at least one embodiment, the first electrical component may receive electrical signals from the tissue using a sensor arranged at the end of the first component, or in the vicinity of the end of the first component, in order to transmit the electrical signals to the proximal end of the first component. By way of one or more embodiments, the signals may be analyzed and/or processed by a processing unit, in order to readjust the stimulation pulses.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
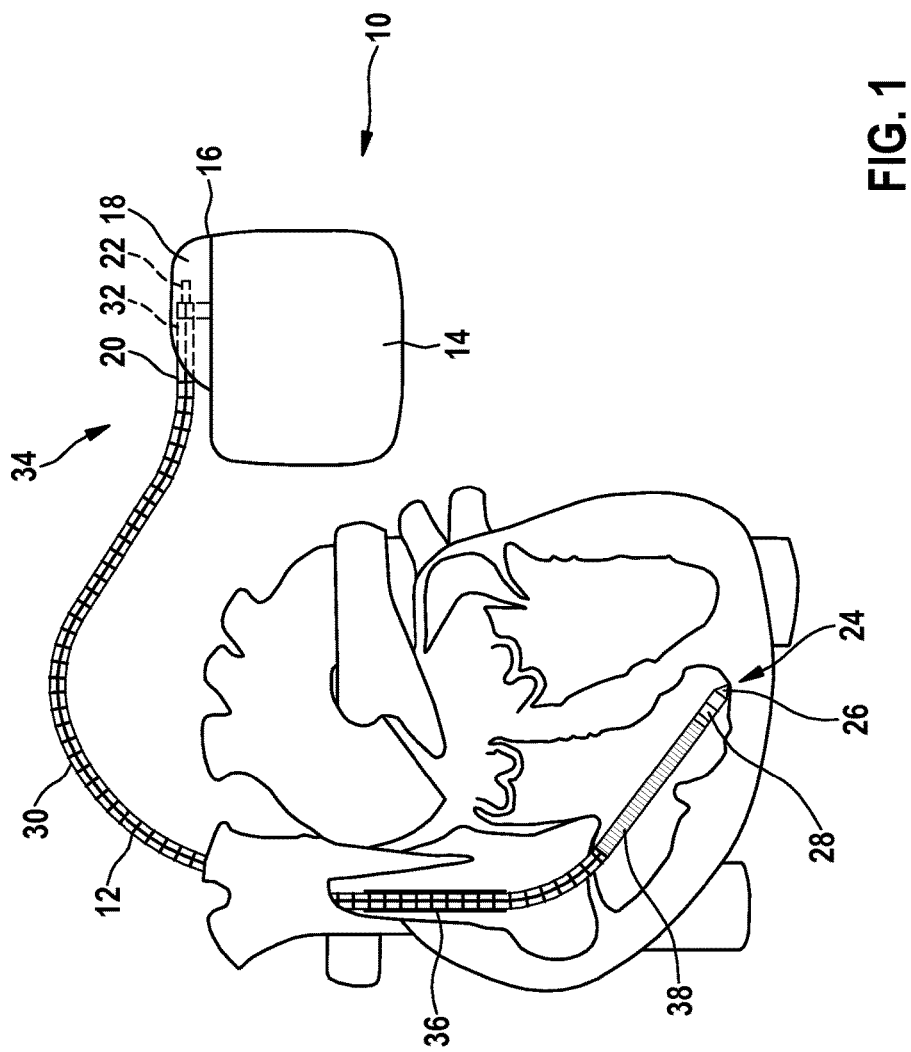
FIG. 1: shows a schematic illustration of an implantable heart stimulator and an implantable electrode line connected thereto.

FIG. 1 shows a schematic illustration of two implantable medical devices namely an implantable heart stimulator 10 and an implantable electrode line 12 electrically connected thereto, according to at least one embodiment of the invention.

In one or more embodiments, the implantable medical device 10 may be or include one or more of a heart stimulator or cardiac pacemaker, such as a ventricular cardiac pacemaker, a defibrillator, a cardioverter-defibrillator (ICD), a purely monitoring device to monitor the heart, a combination of a therapy and monitoring device, an ablation electrode line, or the like.

In at least one embodiment, the implantable medical device 10, for example a heart stimulator may include an electrically conductive metal housing 14, which may be used as a large-area electrode pole. In one or more embodiments, the housing 14 may be made of a non-conductive material. By way of at least one embodiment, the housing 14 includes an outer face 16 with a terminal housing 18, also referred to herein as a header. In one or more embodiments, the terminal housing 18 may include contact sockets 20 with electrical contacts 22 that receive plug contacts. The electrical contacts 22, in at least one embodiment, may be connected by conductors to an electronics system arranged in the housing 14 of the implantable heart stimulator 10.

According to at least one embodiment, the electrode line 12 constitutes a further implantable medical device. In at least one embodiment, a distal end 24 of the electrode line 12 may be located in the apex of a right ventricle of a heart, and may include electrode poles 26 and 28 in the form of a point electrode or tip electrode 26 and in the form of a ring electrode 28 arranged at the distal end or in the vicinity thereof. In one or more embodiments, the electrode poles 26 and 28 may be electrically connected, via one or more electrical functional conductors 30, to a plug contact 32 at a proximal end 34 of the electrode line 12. In at least one embodiment, the electrode poles 26 and 28 may sense electrical potentials of the heart tissue (myocardium) and/or may deliver electrical signals, for example stimulation pulses, to the surrounding heart tissue. According to one or more embodiments, the functional conductors 30 may one or more of transmit the electrical signals used for therapy from the plug contact 32 to the respective electrode pole 26 or 28, and lead signals representing sensed electrical potentials from the respective electrode pole 26 or 28 to the plug contact 32, such that the signals may be used for the basic function of the implantable medical devices 10 and 12. In at least one embodiment, the functional conductors 30 may be surrounded over a large part of their length by an insulating sleeve, such that electrical contact to the tissue of the heart is implemented selectively via the electrode poles 26 and 28. In one or more embodiments, the plug contact 32 may be connected using plug electrical contacts to the electrical contacts 22 of the contact socket in the terminal housing 18 of the implantable heart stimulator 10. As such, in at least one embodiment, signals to or from the electronics system placed in the housing 14 of the implantable medical 10 may be transmitted to or from one or more of the electrode poles 26 and 28. In at least one embodiment, the electrode line 12, for example one type of implantable medical device, may be part of the implantable medical device 10 or may be fixedly connected thereto.

By way of one or more embodiments, electrical functional conductors 30 in the electrode line 12 may be formed in different longitudinal portions as approximately elongate cable conductors, or as helically coiled conductors, or as wire helices. In at least one embodiment, the electrode line 12 may include a large-area proximal electrode pole 36 and a large-area distal electrode pole 38, which may each be formed by at least one bare helically wound wire and may be used as defibrillation electrodes 36 and 38. In one or more embodiments, the electrode line 12 may be used to stimulate and discharge signals to nerves, a brain, and other organs of the body, or to one or more feed lines of implantable sensors.

Figure 2:
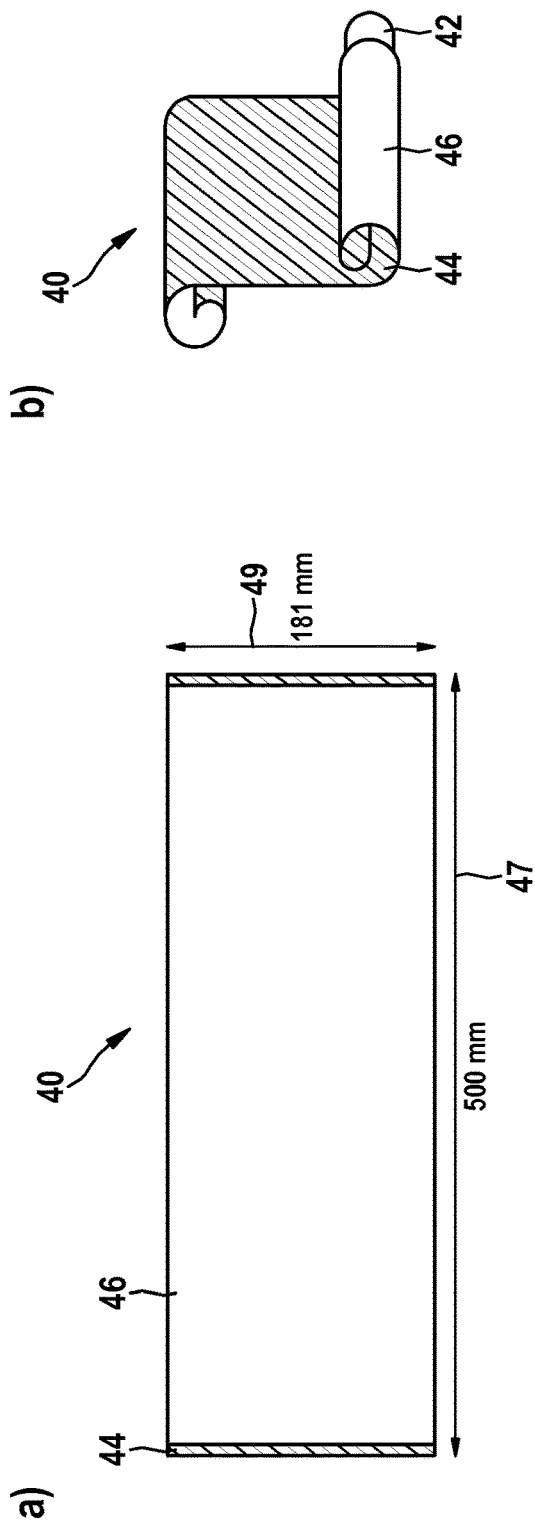
FIG. 2: shows a schematic illustration of a first exemplary embodiment of a sheet of an implantable medical device in an unwound state and in a wound state wound partially over a mandrel.

FIG. 2 shows a schematic illustration of a sheet 40 in the unwound state and in a wound state partially over a mandrel, according to at least one embodiment of the invention. The sheet 40, in at least one embodiment, constitutes a second component of an implantable medical device 12, e.g., may form a portion of the electrode line 12, and may be arranged in an unwound state (as depicted in illustration 2a) and may be in a state partially wound over a mandrel 42 (as depicted in illustration 2b). In at least one embodiment, the sheet 40 may include a plastic layer 44, for example formed from or with a polymer, such as one or more of polyester, polyimide, polyamide, polytetrafluroethylene, polypropylene, polyurethane or the like, and a metal layer 46 applied thereto, for example formed from gold and/or silver. In one or more embodiments, the metal layer 46 may include an electrically conductive material, for example graphene or the like. In one or more embodiments, the plastic layer 44 may include a graphene composite or flurographene. In at least one embodiment, the metal layer 46 may be connected to the plastic layer 44, for example via adhesive bonding, pressing or the like, or may be embedded therein. In at least one embodiment, the sheet 40 may include a length 47 of 500 mm and a width 49 of 181 mm. Thus, sheet 40 as shown in FIG. 2, when situated around at least a portion of the length of an implantable medical device, for example electrode line 12, forms a second component of the electrode line 12 as shown in FIG. 1.

Figure 3:
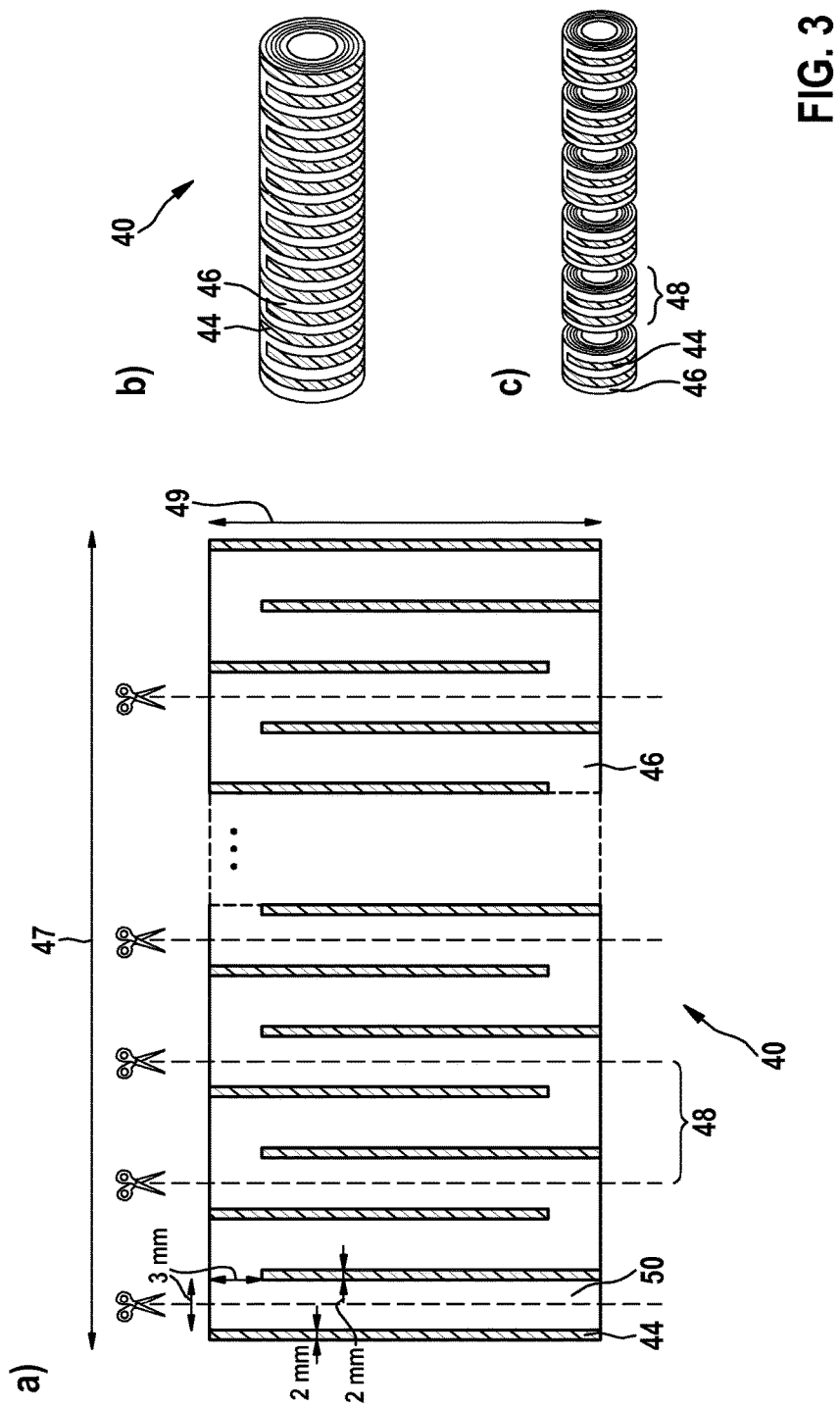
FIG. 3: shows a schematic detailed illustration of the first exemplary embodiment of a sheet of an implantable medical device.

FIG. 3 shows a schematic detailed illustration of a sheet of a second component of an electrode line 12 according to at least one embodiment of the invention. According to one or more embodiments, the sheet 40 may be used as a starting material for miniaturized implantable medical devices by dividing the sheet 40 into sub-portions 48 in the unwound state (as shown in illustration 3a) or in the wound state (as shown in illustrations 3b and 3c). By way of at least one embodiment, the sheet 40 may be divided physically, for example mechanically, thermally (such as with application of heat), by laser or plasma cautery or the like, or chemically, such as using etching or the like. In one or more embodiments, dividing the sheet 40 into a plurality of sub-portions 48 may be done chronologically one after the other or simultaneously. In at least one embodiment, the sheet 40 may be divided along a meander arm 50, wherein shorter identical sub-portions 48 are produced. In one or more embodiments, the sub-portions 48 may be hermetically interconnected by pressure, heat and/or by a solvent. In at least one embodiment, the metal layers 46 of the sub-portions 48 may be electrically interconnected in series.

In one or more embodiments, the metal layer 46 may be applied in different forms to the plastic layer 44. In at least one embodiment, the metal layer 46 may be applied in a meandering manner, wherein a width of the meandering metal layer is 3 mm and is surrounded by plastic layer runners 44 having a width of 2 mm. In one or more embodiments, the sheet 40 may produce a spiraled line (as shown in illustration 3b), or shorter spiraled line portions 48 (as shown in illustration 3c).

Figure 4:
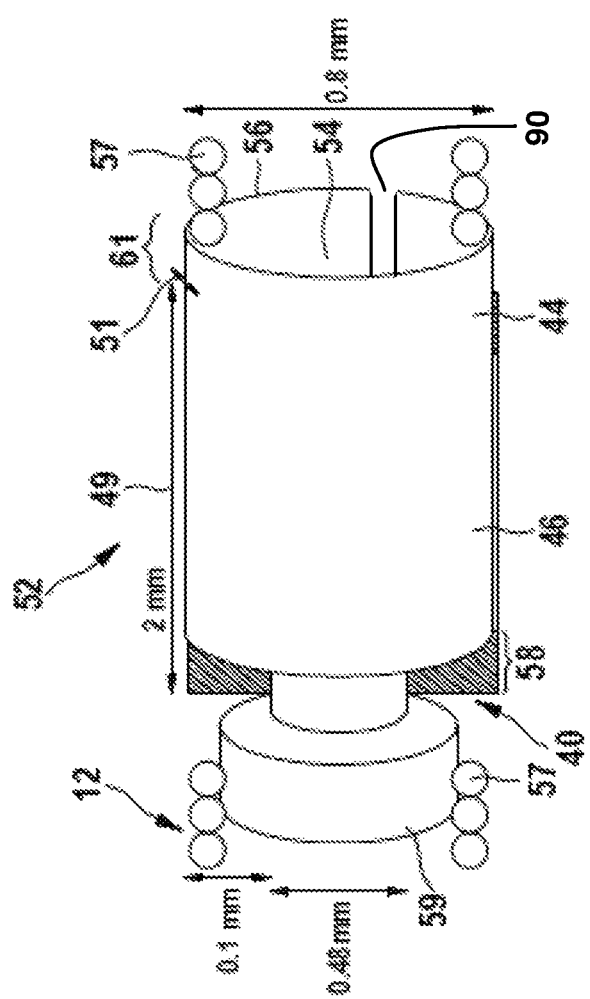
FIG. 4: shows a schematic illustration of a first exemplary embodiment of a sheet strip stop filter.

FIG. 4 shows a schematic illustration of a first exemplary embodiment sheet strip stop filter 52 of an implantable medical device, according to at least one embodiment of the invention. This implantable medical device may couple with or form part of another implantable medical device, for example electrode line 12. In one or more embodiments, the sheet strip stop filter 52 may include an inner cylindrical platinum sleeve 54 electrically connected to the electrode line 12, wherein the sheet 40 may be wound in a spiraled manner about the platinum sleeve 54. The inner platinum sleeve 54, in at least one embodiment, may be part of a functional conductor 30 or may be electrically connected to a functional conductor 30 of the electrode line 12. In one or more embodiments, the metal layer 46 of the sheet 40 may be electrically connected in series to the inner cylindrical platinum sleeve 54. In at least one embodiment, the metal layers 46 may act, using the spiral winding of 76 windings in this example, as inductors with parasitic capacitors connected in parallel thereto. In at least one other embodiment, the number of windings depends on the thickness 51 (as shown in FIG. 5) of the sheet 40, and may be selected to be greater or smaller, and may be matched to features of a site of application of the implantable medical device 12.

According to at least one embodiment, a second outer cylindrical platinum sleeve 56 with an inner diameter corresponding to the outer diameter of the wound sheet 40 may surround the wound sheet 40. In one or more embodiments, the outer cylindrical platinum sleeve 56 may be electrically connected in series to at least one metal layer 46 of the sheet 40. In at least one embodiment, part of the sheet 40 may be guided outwardly about the outer platinum sleeve 56 through a slit 90 in the outer platinum sleeve 56. In one or more embodiments, the inner platinum sleeve 54 may be a slit sleeve. According to at least one embodiment, the sleeves 54 and 56 may be made of or include one or more of gold, silver, carbon nanotube composite, plastic or another conductive or non-conductive material. In at least one embodiment, only one of the sleeves 54 or 56 may include a conductive material, whereas the other sleeve 54 or 56 may be formed from or include a non-conductive material. In one or more embodiments, the sleeves 54 or 56 may be formed as, or include, capillary tubes made of plastic, wherein the same material for the sleeves 54 and 56 may be used for the plastic layer 44, such that a connection of the implantable medical device 12 may be simplified. In at least one embodiment, the use of the same material for the inner cylindrical sleeve 54 and the plastic layer 44 may simplify the mechanical connection to the implantable medical device 12.

According to at least one embodiment of the invention, the electrical line in the form of a wire helix 57 may surround an inner insulation sleeve 59 of the electrode line 12, which electrically insulates an inner electrical line connected to the inner platinum sleeve 54 from the wire helix 57. In at least one embodiment, the inner electrical line may include a wire helix.

Figure 5:
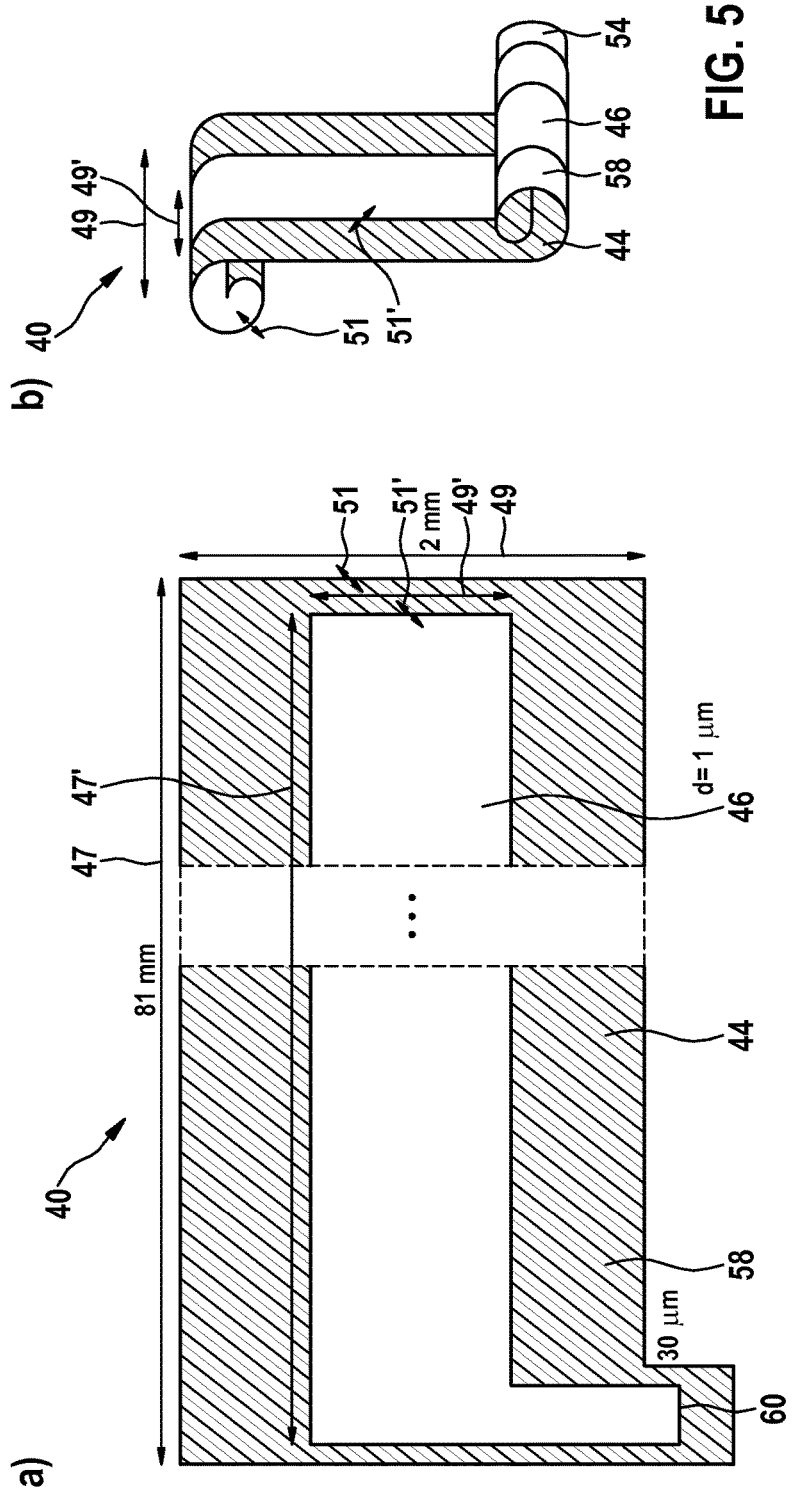
FIG. 5: shows a schematic illustration of a second exemplary embodiment of a sheet of an implantable medical device in the unwound state and in the wound state partially over a platinum sleeve.

By way of one or more embodiments, the plastic layer 44 of the sheet 40 may be formed from, or include, polyester, and may have a width 49 of 2 mm, a length 47 of 81 mm, and a thickness 51 of 1.2 μm or 1 μm (as shown in FIG. 5). In at least one embodiment, the metal layer 46 of the sheet 40 may include gold and may be arranged centrally on the plastic layer 44, and may have a width 49' of 1.8 mm, a length 47' of slightly less than 81 mm, and a thickness 51' of 0.300 μm, such that a non-conductive plastic edge 58 may be produced on the sheet 40 (as shown in FIG. 5). The width 49' of the metal layer 46, in at least one embodiment, may be smaller than the width 49 of the sheet 40 or plastic layer 44. In one or more embodiments, the metal layer 46 may be introduced within two plastic layers 44 in a sandwich construction. In at least one embodiment, the thickness 51' of the metal layer 46 may be smaller than its width 49' (as shown in FIG. 5). In at least one embodiment, the sheet 40 may have a length of 14 cm. Other dimensions depending on the specific implementation desired are in keeping with the spirit of the invention and all examples described herein with respect to any figure or embodiment are not to be taken in any limiting sense.

According to one or more embodiments, the inner platinum sleeve 54 may be slit and may include an inner diameter of 0.4 mm, an outer diameter of 0.48 mm or 0.5 mm, and a length of 2.5 mm. In at least one embodiment, the length of the platinum sleeve 54 may be 0.5 mm greater than the width 49 of the sheet 40, and therefore part of the platinum sleeve 54 about which the sheet 40 is wound remains free and may be connected to the inner electrical line, such as a wire helix of an electrode. In at least one embodiment, the platinum sleeve 54 may be, or may include, an electrode. In one or more embodiments, the metal layer 46 of the sheet 40 may be electrically connected via a contact 60 (as shown in FIG. 5) to the inner platinum sleeve 54. In at least one embodiment, the contact 60 may have a width of 70 μm and may be distanced from the outer edge of the sheet 40 by 30 μm or approximately 30 μm. In at least one embodiment, the slit formation of the inner platinum sleeve 54 may prevent a short circuit of a winding, which may severely reduce inductance.

By way of one or more embodiments, winding the sheet 40 perpendicular to the width 49 thereof about the platinum sleeve 54 may produce an outer diameter of the wound sheet 40 of 0.7 mm. In at least one embodiment, the sheet 40 may be surrounded by an outer platinum sleeve 56 with an inner diameter of 0.68 mm or 0.7 mm, an outer diameter of 0.8 mm, and a length of 2.5 mm, wherein the sheet 40 may be completely covered, and 5 mm of the sheet 40 may be guided through a slit in the sleeve. In one or more embodiments, the metal layer 46 of the sheet 40 may be electrically connected to the outer sleeve of the outer platinum sleeve 56. In at least one embodiment, a proportion 61 of 0.5 mm of the outer platinum sleeve 56 may reach beyond the width 49 of 2 mm of the sheet 40, wherein the outer platinum sleeve may be electrically connected to a continuing wire helix 57 beneath the sleeve. In one or more embodiments, the slit outer platinum sleeve 56 may taper to an outer diameter of 0.5 mm after a cylindrical portion of 2 mm, which surrounds the sheet 40, such that the wire helix 57 may be electrically connected on the outer face of the outer platinum sleeve 56.

According to at least one embodiment of the invention, a smaller outer diameter of the implantable medical device 52 may enable flexible contacting along the entire wire helix 57, without the need for further structural modifications of the electrode 26 and/or 28.

By way of one or more embodiments, the sheet strip stop filter 52 or the implantable medical device 52 may be arranged at the distal end 24 or in the vicinity of the distal end 24 of the electrode 26 in order to reduce heating of the electrode 26 and of the tissue surrounding the electrode 26 in an effective manner. In at least one embodiment, the implantable medical device 52 may be arranged in the direct vicinity of the ring electrode 28, such as immediately distally of the ring electrode 28, wherein additional mechanical protection may be achieved.

FIG. 5 shows a schematic illustration of a second exemplary embodiment of a sheet 40, for example implantable medical device 40, in the unwound state and in the wound state partially over a platinum sleeve 54, according to at least one embodiment of the invention. Illustration 5a shows a second exemplary embodiment of sheet 40 with a metal layer 46 running centrally along the length 47 of the sheet 40 and having a length 47', wherein the sheet 40 may be applied to a plastic layer 44. In at least one embodiment, the metal layer 46 may be electrically connected via the contact 60 to the inner platinum sleeve 54. As shown in illustration 5b, the sheet 40 may be wound partially on an inner platinum sleeve 54 and may be electrically connected thereto. In at least one embodiment, the metal layer 46 on the sheet 40 may include two non-conductive plastic edges 58 along the direction of the longitudinal axis of the platinum sleeve 54.

Figure 6:
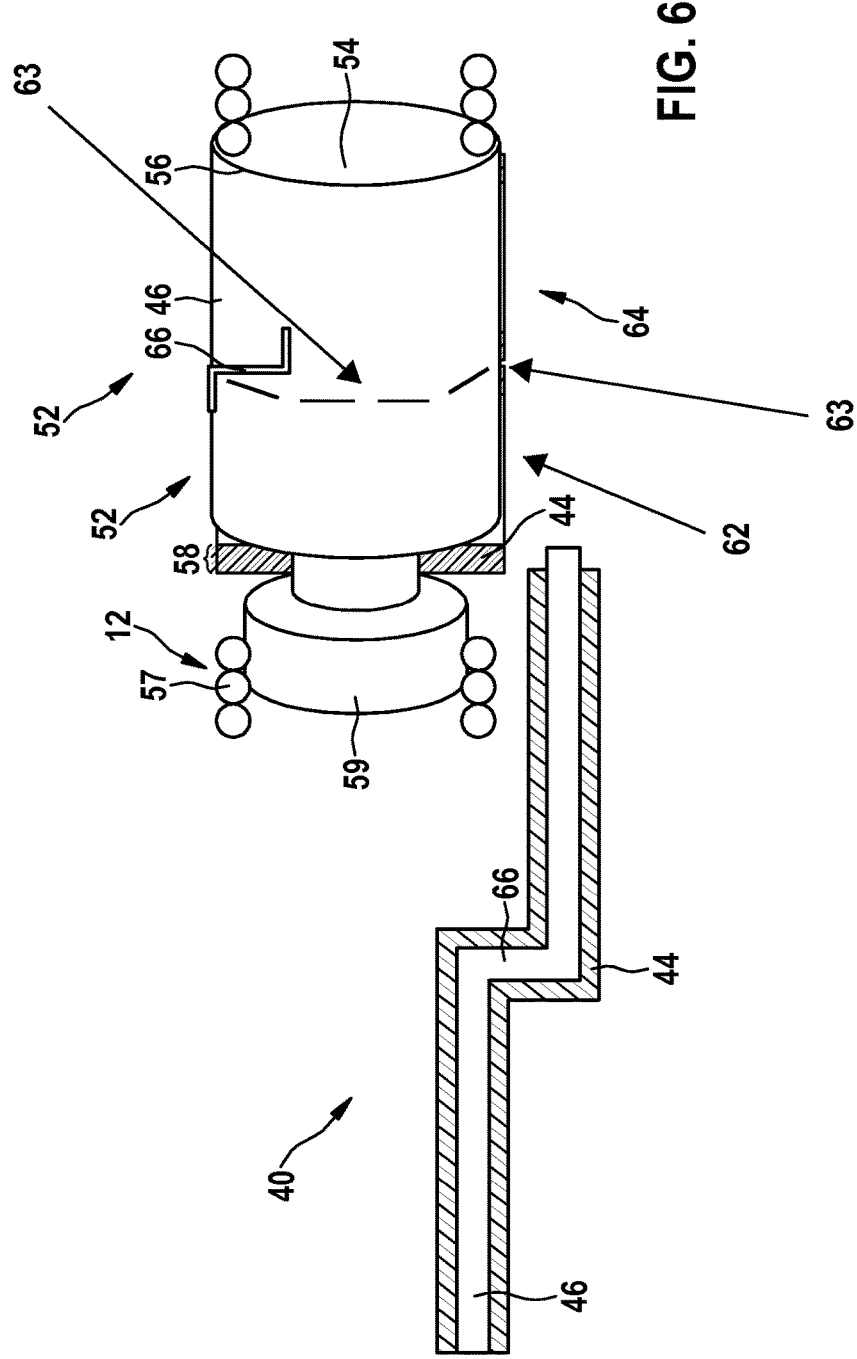
FIG. 6: shows a schematic illustration of the second exemplary embodiment of a sheet of an implantable medical device with a sheet strip stop filter.

FIG. 6 shows the second exemplary embodiment of a sheet 40, for example a sheet strip stop filter 52, e.g., an implantable medical device 52, according to at least one embodiment of the invention. In at least one embodiment, two spirally wound sheets 40 may surround an inner platinum sleeve 54 and may be surrounded by an outer platinum sleeve 56. In one or more embodiments, a proximal sheet 62 may be electrically connected to the outer wall of the inner platinum sleeve 54. According to at least one embodiment, a second distal sheet 64 may be electrically connected at its proximal end to the proximal sheet 62, for example with electrical connection 66, and at its distal end to the outer platinum sleeve 56, wherein the platinum sleeves 54 and 56 may be connected in series to the sheets 62 and 64. According to at least one embodiment there may be a gap 63 between the opposing flanks of sheets 62 and 64 or the electrically isolated opposing flanks of sheets 62 and 64 may be in physical contact. In at least one embodiment, the series connection of a plurality of sheets 40, which may serve as filters, allow for a desired frequency response. In one or more embodiments, the series connection produced by sheets 40 may be cut in a step-shaped manner, wherein, after each wound sheet 40, an electrically conductive web 66 may be guided back from the metal layer 46 of the sheet 62 in the vicinity of the outer wall of the inner platinum sleeve 54 in order to electrically connect the inner platinum sleeve 54 to a metal layer 46 of the axially adjacent sheet 64. In at least one embodiment, the sheet 64, following the first sheet 62, may not be electrically connected to the inner platinum sleeve 54, as such a connection may lead to a connection in parallel. By way of one or more embodiments, cylindrical faces of the axially adjacent sheets 62 and 64, or the sub-portions 62 and 64, may be hermetically interconnected by one or more of pressure, heat and a solvent in order to hermetically seal the sheet strip stop filter 52.

According to at least one embodiment, the distal sheet 64 may be electrically connected to the inner platinum sleeve 54, wherein a bandwidth of the implantable medical device 12 may be adapted. Due to the various configurations of the sheet strip stop filter 52, bandwidths and pass frequencies may be adjusted such that a cooling effect may occur in a number of frequency bands, and a manufacturing tolerance may be increased.

Figure 7:
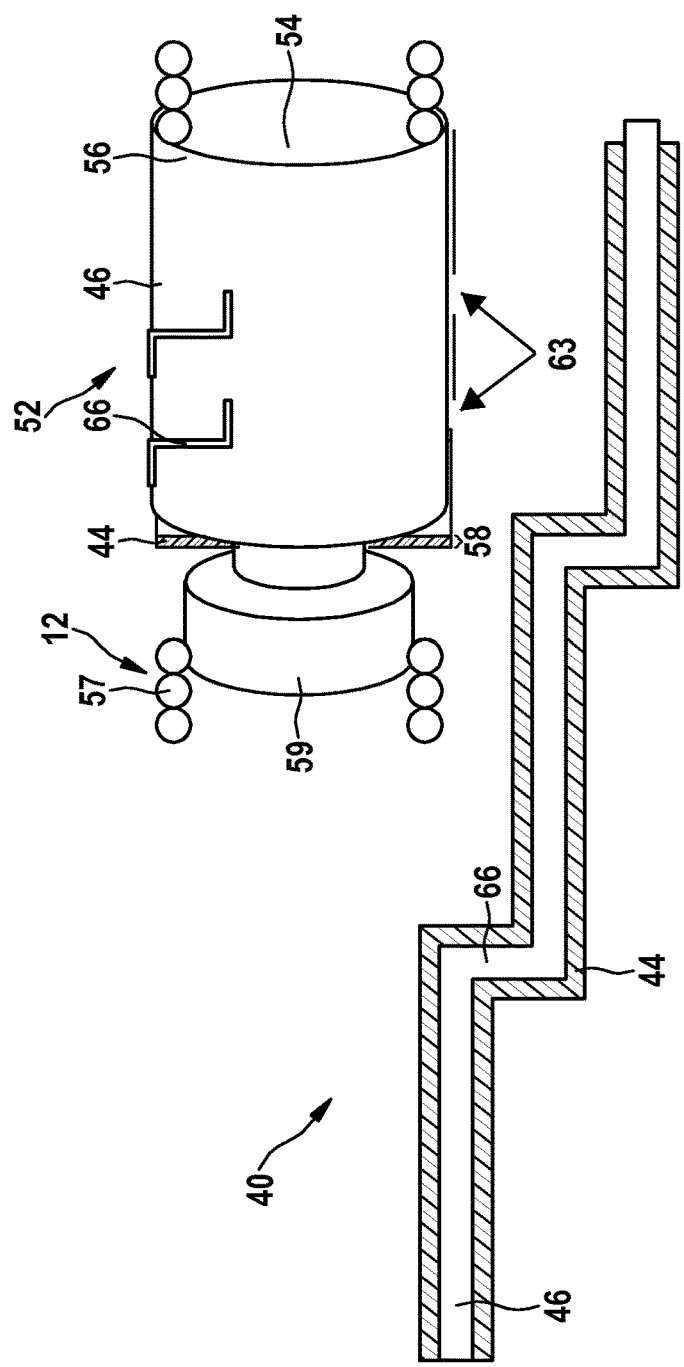
FIG. 7: shows a second schematic illustration of the second exemplary embodiment of a sheet of an implantable medical device in a third exemplary embodiment of a sheet strip stop filter.

FIG. 7 shows a second exemplary embodiment of the sheet 40 of an implantable medical device 52 in a third exemplary embodiment of a sheet strip stop filter 52, according to at least one embodiment of the invention. In one or more embodiments, the sheet strip stop filter 52 may be identical to the sheet strip stop filter 52 of FIG. 6, as discussed above, however may include three sheet portions, instead of two sheet portions, connected in series.

By way of at least one embodiment, the exact geometrical dimensions of the flexible sheet strip stop filter 52 may comply with, and adapt to, one or more of the outer restrictions and dimensions of the site of use (maximum outer diameter $r_2$, minimum inner diameter $r_1$ and maximum length b), the material selection of the plastic layer 44 or of the sheet substrate, and the shape and material of the metal layer 46, metallization, and a desired resonance frequency.

One or more embodiments of the invention may include a sheet strip stop filter 52, such as the sheet strip drop filter 52 illustrated in FIG. 7, formed from sub-portions 48 of the sheet 40 (as shown in FIG. 2 and FIG. 3) with a meandering metal layer 46. In at least one embodiment, the resonance frequency of the sheet strip stop filter 52 may be represented as:

$$f = \frac{1}{2\pi}\sqrt{\frac{1}{LC} - \frac{R^2}{L^2}};$$

with an inductance L and a capacitance C, which may be estimated from the parasitic capacitances between the spiral arms, and with a resistance R of the sheet strip stop filter 52. In at least one embodiment, the capacitance may be calculated from the capacitance in barrel capacitors connected in series, represented as:

$$\frac{1}{C} = \sum_n \frac{1}{C_n} \text{ with } C_n = 2\pi\varepsilon_0\varepsilon_r \frac{b}{\lg\left(\frac{r_1 + (n-1)d}{r_1 + nd}\right)};$$

with a dielectric constant $\varepsilon_0$, a relative permittivity $\varepsilon_r$ of the plastic layer 44, a width b of the meander arm 50 of the metal layer 46, a thickness d of the sheet 40, and a number of spiral windings n of the sheet 40.

According to one or more embodiments, inductance of the spiral sheet strip stop filter 52 may be estimated using the following formula $$\left(r = \left(\frac{r_1 + r_2}{2}\right)\right)$$

in cm, where $r_1$ is the inner diameter and $r_2$ is the outer diameter):

$$L = r^2 n^2 / 20r + 28(r_2 - r_1).$$

At least one embodiment of the invention may be incorporated in a pacemaker electrode, or any other implantable medical device electrode 12, for frequencies around 64 MHz, and may include a plastic layer 44 in the form of a polymer sheet formed from polyester with a thickness 51 of d=1.855 µm and with a relative permittivity of $\varepsilon_r \sim 3$, and a metal layer 46 formed from silver with a thickness 51' of d=0.045 µm. In at least one embodiment, the sheet 40 may include an outer diameter of $r_2$=780 µm, an inner diameter of $r_1$=500 µm, a length 47 of b=3 mm, and 74 windings.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

| | |
|---|---|
| 10 | cardiac pacemaker |
| 12 | electrode line |
| 14 | housing of the cardiac pacemaker |
| 16 | outer face of the cardiac pacemaker |
| 18 | terminal housing |
| 20 | contact sockets |
| 22 | electrical contacts of the cardiac pacemaker |
| 24 | distal end of the electrode line |
| 26 | point/tip electrode |
| 28 | ring electrode |
| 30 | functional conductor |
| 32 | plug contact of the electrode line |
| 34 | proximal end of the electrode line |
| 36 | large-area proximal electrode pole |
| 38 | large-area distal electrode pole |
| 40 | sheet |
| 42 | mandrel |
| 44 | plastic layer |
| 46 | metal layer |
| 47 | length |
| 48 | sub-portion |
| 49 | width |
| 50 | meander arm |
| 51 | thickness |
| 52 | sheet strip stop filter |
| 54 | inner cylindrical platinum sleeve |
| 56 | outer cylindrical platinum sleeve |
| 57 | wire helix |
| 58 | plastic edge of the sheet |
| 59 | inner insulation sleeve |
| 60 | contact on the metal layer |
| 61 | part of the outer platinum sleeve |
| 62 | proximal sheet |
| 63 | gap between sheets 62 and 64 |
| 64 | distal sheet |
| 66 | electrically conductive web |

What is claimed is:
1. An implantable medical device comprising:
   at least one elongate electrical line comprising
   a first electrical component,
   a second component, and
   a third component;

wherein the first electrical component comprises a functional conductor;
wherein the second component comprises a composite formed from at least one metal layer and at least one flexible plastic layer connected to the at least one metal layer;
wherein the first electrical component and the at least one metal layer of the second component are electrically connected, wherein at least one of the at least one metal layer of the second component is connected in series to the first electrical component;
wherein the third component is electrically connected to the at least one metal layer of the second component;
wherein the first electrical component is surrounded by the second component;
wherein the third component comprises a slit sleeve made of a conductive material with an inner diameter of the slit sleeve corresponding to the outer diameter of the second component that is wound;
wherein the second component is surrounded in part by the slit sleeve;
wherein the at least one flexible plastic layer of the second component comprises two lateral edges; and,
wherein the two lateral edges are hermetically interconnected by one or more of pressure, heat and a solvent.

2. The implantable medical device as claimed in claim 1, further comprising an electrode line, wherein the electrode line comprises the at least one elongate electrical line or a portion of the at least one elongate electrical line, and wherein the electrode line is configured to connect to a therapy device, a monitoring device or a therapy and monitoring device.

3. The implantable medical device as claimed in claim 1, wherein the at least one metal layer of the second component comprises a first width, and the at least one flexible plastic layer comprises a second width, such that the first width of the at least one metal layer is smaller than the second width of the at least one flexible plastic layer, and wherein the two lateral edges comprise a second plastic layer or the at least one plastic layer.

4. The implantable medical device as claimed in claim 1, wherein the at least one metal layer of the second component is meandered, such that the at least one metal layer is configured to be applied to the at least one flexible plastic layer in a meandering manner.

5. The implantable medical device as claimed in claim 4, further comprising a meander arm, wherein the second component comprises at least two axially divided sub-portions divided along the meander arm as at least two separate second components comprising a first sub-portion and a second sub-portion with at least two separate metal layers, and wherein at least one separate metal layer of the first sub-portion is connected in series to at least one separate metal layer of the second sub-portion.

6. The implantable medical device as claimed in claim 1, wherein the second component is spiraled and configured to be wound in a spiraled manner about the first electrical component.

7. The implantable medical device as claimed in claim 1, wherein the second component is surrounded by the third component.

8. The implantable medical device as claimed in claim 1, wherein the at least one metal layer comprises a first width and a first thickness, wherein the first thickness is smaller than the first width.

9. The implantable medical device as claimed in claim 1, wherein the at least one flexible plastic layer comprises at least one polymer.

10. A method for producing an implantable medical device comprising:
providing at least one elongate electrical line comprising
a first electrical component,
a second electrical component, and,
a third electrical component,
wherein the first electrical component comprises a functional conductor;
providing the second component as a composite comprising at least one metal layer and at least one flexible plastic layer connected to the at least one metal layer; and,
electrically connecting the at least one metal layer of the second component to the first electrical component,
wherein the at least one metal layer of the second component is connected in series to the first electrical component,
wherein the third component is electrically connected to the at least one metal layer of the second component,
wherein the first electrical component is surrounded by the second component,
wherein the third component comprises a slit sleeve made of a conductive material with an inner diameter of the slit sleeve corresponding to the outer diameter of the second component that is wound,
wherein the second component is surrounded in part by the slit sleeve, and
wherein the at least one flexible plastic layer of the second component comprises two lateral edges; and,
hermetically interconnecting the two lateral edges by one or more of pressure, heat and a solvent.

11. The method for producing an implantable medical device as claimed in claim 10, further comprising physically dividing the second component or a portion of the second component into at least two axially arranged sub-portions comprising a first sub-portion and a second sub-portion with at least two separate metal layers.

12. The method for producing an implantable medical device as claimed in claim 10, further comprising chemically dividing the second component or a portion of the second component into at least two axially arranged sub-portions comprising a first sub-portion and a second sub-portion with at least two separate metal layers.

13. The method for producing an implantable medical device as claimed in claim 11, wherein the at least two axially arranged sub-portions comprise cylindrical faces, and wherein the cylindrical faces are hermetically interconnected by one or more of pressure, heat and a solvent.

14. The method for producing an implantable medical device as claimed in claim 11, further comprising adjacently arranging and electrically conductively interconnecting in series at least one separate metal layer of the first sub-portion and at least one separate metal layer of the second sub-portion.

* * * * *